United States Patent [19]

Ledford et al.

[11] Patent Number: 6,036,718
[45] Date of Patent: Mar. 14, 2000

[54] BLADDERLESS BLOOD PRESSURE CUFF

[75] Inventors: James Ledford, Asheville; Robert Drake, Hendersonville, both of N.C.; Lafoy Ellenburg, Seneca, S.C.; Gary Jarvis; Edward L. Peart, both of Arden, N.C.

[73] Assignee: Welch Allyn, Inc., Skaneateles, N.Y.

[21] Appl. No.: 09/109,779

[22] Filed: Jul. 2, 1998

[51] Int. Cl.⁷ .................................................. A61B 17/00
[52] U.S. Cl. ........................................ 606/202; 600/485
[58] Field of Search .................................... 606/202, 190; 604/396, 96; 128/2; 601/151–152; 600/480, 481, 485

[56] References Cited

U.S. PATENT DOCUMENTS

| | | |
|---|---|---|
| 2,467,133 | 4/1949 | Irons . |
| 2,660,660 | 11/1953 | Hauteville . |
| 2,865,790 | 12/1958 | Baer . |
| 3,046,179 | 7/1962 | Stallard . |
| 3,126,307 | 3/1964 | Drittenbass . |
| 3,391,434 | 7/1968 | Girard . |
| 3,393,119 | 7/1968 | Dugan . |
| 3,535,184 | 10/1970 | Schwartz . |
| 3,576,690 | 4/1971 | Staats et al. . |
| 3,616,028 | 10/1971 | Miller et al. . |
| 3,633,567 | 1/1972 | Sarnoff ........................................ 128/2 |
| 3,647,607 | 3/1972 | Hillers . |
| 3,654,931 | 4/1972 | Hazlewood . |
| 3,762,979 | 10/1973 | Hanel et al. . |
| 3,773,036 | 11/1973 | Weyer . |
| 3,862,870 | 1/1975 | Suda et al. . |
| 3,935,361 | 1/1976 | Dorfman et al. . |
| 3,994,454 | 11/1976 | Worsham . |
| 4,033,337 | 7/1977 | Raczkowski . |
| 4,156,425 | 5/1979 | Arkans . |
| 4,216,046 | 8/1980 | Hackert . |
| 4,268,338 | 5/1981 | Peterson . |
| 4,338,150 | 7/1982 | Weeks . |
| 4,402,312 | 9/1983 | Villari et al. . |
| 4,410,575 | 10/1983 | Obayashi et al. . |
| 4,470,857 | 9/1984 | Casalou . |
| 4,624,244 | 11/1986 | Taheri . |
| 4,643,932 | 2/1987 | Daniels . |
| 4,662,037 | 5/1987 | Provost et al. . |
| 4,761,318 | 8/1988 | Ott et al. . |
| 4,838,276 | 6/1989 | Nagai et al. . |
| 4,857,129 | 8/1989 | Jensen et al. . |
| 4,859,524 | 8/1989 | Kim et al. . |
| 4,894,060 | 1/1990 | Nestegard . |
| 4,950,347 | 8/1990 | Futagawa . |
| 5,036,838 | 8/1991 | Sherman . |
| 5,061,540 | 10/1991 | Cripps et al. . |
| 5,095,894 | 3/1992 | Marble . |
| 5,098,419 | 3/1992 | Gold ........................................ 604/396 |
| 5,101,830 | 4/1992 | Duffy et al. . |
| 5,146,932 | 9/1992 | McCabe . |
| 5,179,957 | 1/1993 | Williams . |
| 5,193,549 | 3/1993 | Bellin et al. . |
| 5,260,015 | 11/1993 | Kennedy . |
| 5,277,737 | 1/1994 | Li et al. . |
| 5,392,782 | 2/1995 | Garrett . |
| 5,513,643 | 5/1996 | Suite . |
| 5,626,556 | 5/1997 | Tobler et al. . |
| 5,779,728 | 7/1998 | Lundsford et al. ...................... 606/190 |
| 5,792,106 | 8/1998 | Mische ........................................ 604/96 |

*Primary Examiner*—Michael Buiz
*Assistant Examiner*—Jonathan D. Goldberg
*Attorney, Agent, or Firm*—Wall Marjama Bilinski & Burr

[57] ABSTRACT

A blood pressure cuff having a pair of flexible gas-impermeable sheets wherein each of the sheets has an inner and an outer side and wherein the inner sides are placed in contact and the edges of the sheets are fused along a periphery thereof to form an interior chamber. At least one hook fastener portion is disposed on one outer side of one of the sheets and at least one loop portion is disposed on an outer side of the other of the sheets. A conduit means is attached to one of the flexible sheets for connecting to a source of pressurized fluid for allowing inflation and deflation of the interior chamber. The sheets are fused together by RF welding along a perimeter of one outer side of one of the sheets. The hook fastener portion, the loop portion, and the conduit means are each RF welded to an outer side of one of said sheets.

10 Claims, 3 Drawing Sheets

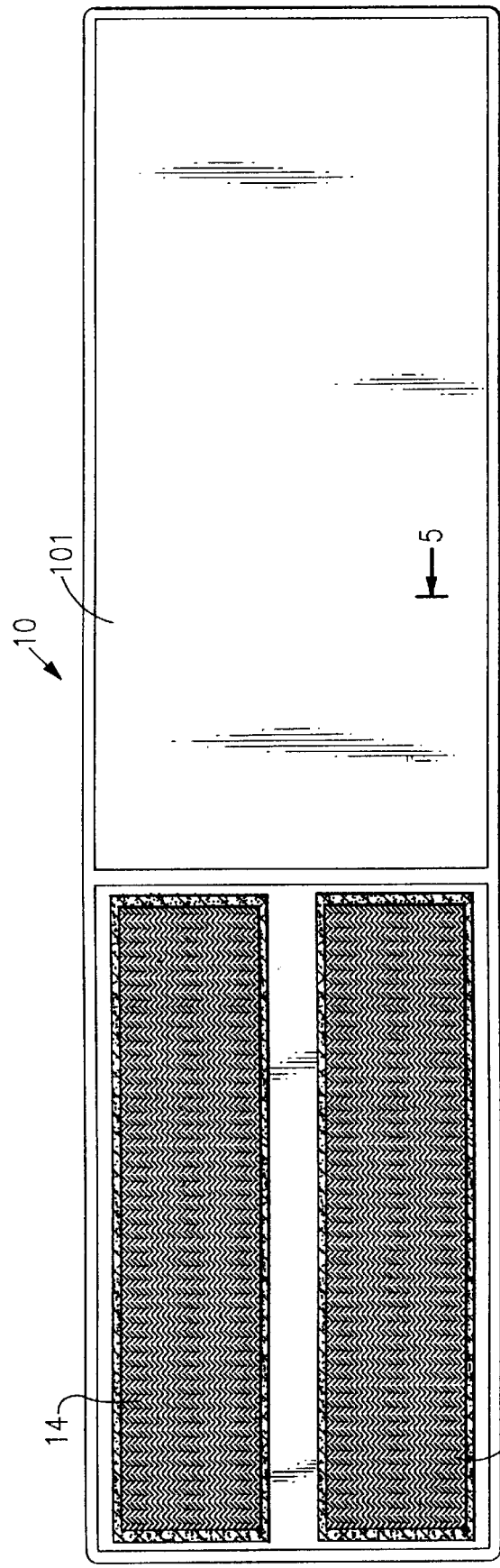
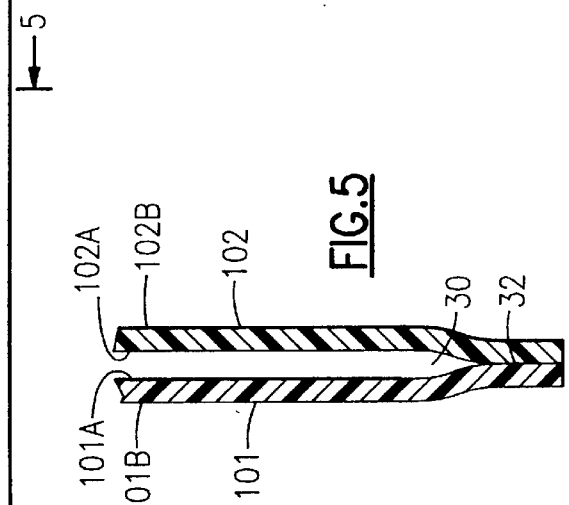

BLADDERLESS BLOOD PRESSURE CUFF

BACKGROUND OF THE INVENTION

This invention relates to a blood pressure monitoring device and specifically relates to an improved cuff for a sphygmomanometer and a method of manufacturing the same.

The measurement of blood pressure is a strong tool in the diagnosis of many medical conditions and diseases, for example heart disease. The measurement of blood pressure is performed as part of a standard physical examination and the blood pressure of seriously ill patients is monitored on a very frequent basis. The blood pressure of a patient is usually determined by the use of a sphygmomanometer. The sphygmomanometer is used by wrapping an inflatable cuff around an arm or leg. The cuff is inflated by a pneumatic bulb that is connected to the cuff by a tube or tubes. The cuff is inflated to provide a certain amount of pressure on the artery in the arm or leg, typically just enough pressure to restrict the blood flow in a major artery in the arm or leg. The health care provider utilizes a stethoscope to listen for blood flow in the artery while the cuff is slowly deflated. The cuff is deflated by allowing air to slowly flow out of the tube. The health care provider hears the blood flow resume while simultaneously reading a gauge on the sphygmomanometer which has predetermined pressure measurements thereon. The pressure in the cuff is continuously reduced until the health care provider can no longer hear the blood flow. The health care provider thereby determines the systolic and diastolic blood pressure of the patient.

There are numerous configurations of blood pressure cuffs that are known in the art, including the cuff described in U.S. Pat. No. 5,101,830 to Duffy et al., which describes a polyurethane coated nylon sheet folded medially to form the pressure cuff. The urethane coated surface forms the inner surface of the inflation chamber. A hook and loop fastener assembly is fused to the cuff and an inflation fitting is also fused to the interior of the pressure chamber.

Another blood pressure cuff configuration is described in U.S. Pat. No. 5,392,782 to Garrett, which describes a disposable cuff and method of production. Garrett discloses a disposable medical pressure cuff that includes one side made from a flexible non-porous plastic sheet and the other side made from a woven fabric sheet that presents a fleecy surface to provide comfort when the cuff is in use.

The methods of manufacture and the resulting configurations that are known in the art have some disadvantages. For example, the plasticized materials that are used to manufacture some of the cuffs present a clammy, uncomfortable feel to the patient. Fleece type disposables are expensive to produce and to any users who must constantly replace. In addition, the configurations of some of the components that are found on the cuffs also tend to make manufacturing the cuffs more burdensome and therefore more expensive. An additional problem that exists with blood pressure cuffs is biological cross-contamination between patients due to repeated use on different patients.

OBJECTS AND SUMMARY OF THE INVENTION

It is, therefore, an object of the invention to provide an easier method of manufacturing a bladderless blood pressure cuff.

It is a further object of the invention to provide a more economical method of manufacturing a bladderless blood pressure cuff.

It is an object of the invention to provide a bladderless blood pressure cuff that maintains a comfortable fit on the patient.

It is an additional object of the invention to provide a reusable blood pressure cuff that limits the amount of cross-contamination between successive patients.

These and other objects are attained by providing a blood pressure cuff having a pair of flexible gas-impermeable sheets. Each of the sheets having an inner and an outer side, wherein the inner sides are placed in contact and the edges of the sheets are fused along a periphery thereof to form an interior chamber. At least one hook fastener portion is disposed on one outer side of one of the sheets and at least one loop portion is disposed on an outer side of the other of the sheets. A conduit means is attached to one of the flexible sheets for connecting to a source of pressurized fluid for allowing inflation and deflation of the interior chamber. The sheets are fused together by RF welding along a perimeter of one outer side of one of the sheets. The hook fastener portion, the loop portion, and the conduit means are each RF welded to an outer side of one of said sheets.

DESCRIPTION OF THE DRAWINGS

The objects and features of the present invention will be more fully understood with reference to the drawings wherein:

FIG. 2 is a plan view of the back side the bladderless blood pressure cuff.

FIG. 5 is a cut-away view along line 5 in FIG. 2.

DETAILED DESCRIPTION OF THE INVENTION

Figure 1:
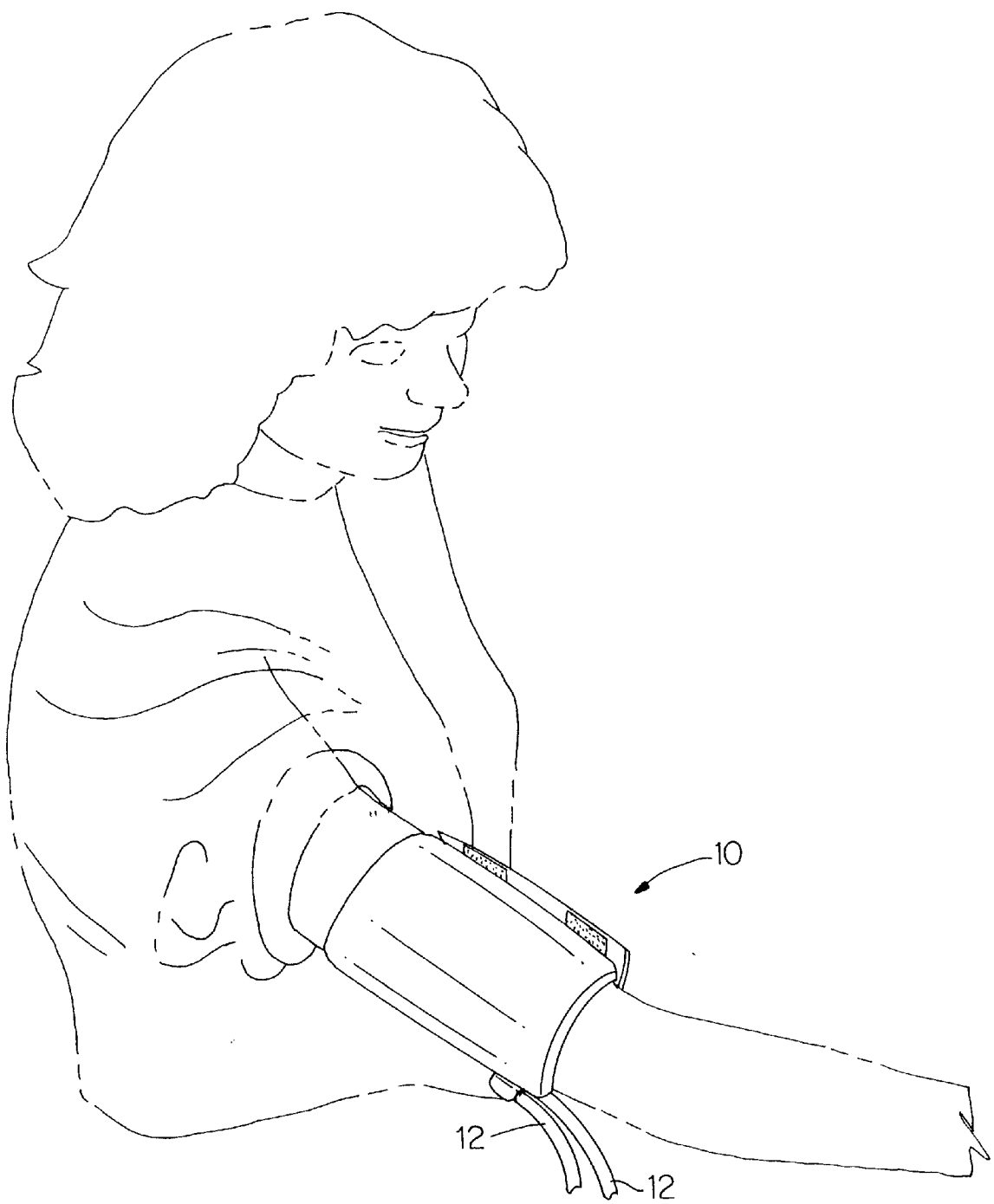
FIG. 1 is a view of the bladderless blood pressure cuff in use on the arm of a patient.

Referring to FIG. 1, there is shown a bladderless blood pressure cuff 10 that embodies the invention disclosed and claimed herein. The cuff 10 is shown in use, wherein it is wrapped and fastened about the arm of a patient. In use, the cuff 10 is connected by tubes 12 to a pneumatic bulb (not shown) or other means for inflating/deflating the cuff 10. The cuff 10 combined with the pneumatic means, connecting means and a pressure gauge constitute a sphygmomanometer.

Figure 3:
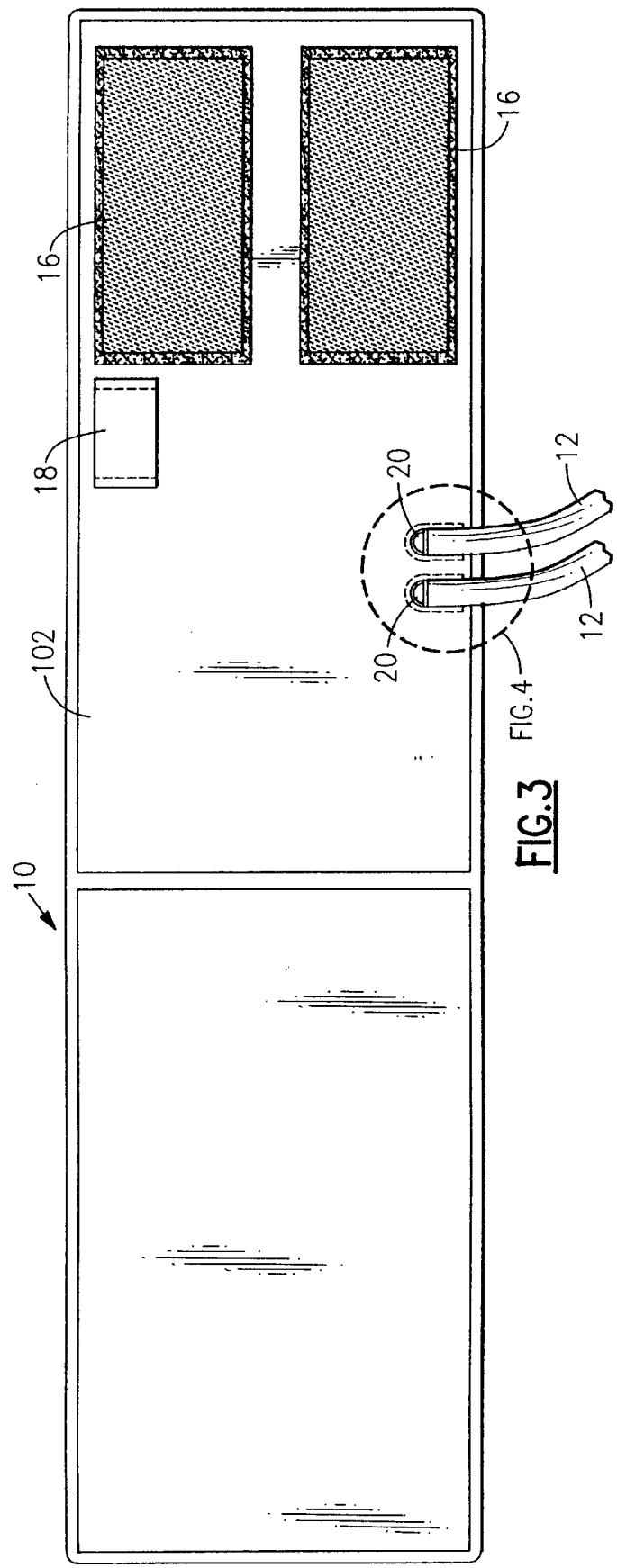
FIG. 3 is a plan view of the front side of the bladderless blood pressure cuff.

Referring now to FIG. 2., there is shown the back side 101 of the blood pressure cuff 10. The cuff 10 is constructed of two sheets of material, preferably urethane coated nylon or polyester, which are RF welded to each other about their perimeters, as will be described in more detail below. The back side 101 of the pressure cuff comprises one of the sheets of coated nylon. The cuff 10 has one or more hook/loop fasteners 14 which are RF welded to the back side 101 in a position to allow for fastening of the cuff 10 about the arm or leg of a patient. The hook/loop fasteners 14 are used in conjunction with the complementary hook/loop fasteners 16 which are shown in FIG. 3, wherein the front side 102 of the blood pressure cuff 10 is depicted. The front side 102 comprises the other sheet of coated nylon and the complementary hook/loop fasteners 16 are RF welded to the front side 102.

An additional feature of the preferred embodiment of the invention is a cleat 18 which is RF welded to the front side 102. The cleat 18 is a common feature known in the art which allows certain types of hand-held sphygmomanometers fitted with spring clips (not shown) to be attached to the cuff 10. This feature allows for the diagnostician to have a free hand during the course of taking the blood pressure measurement.

Referring to FIG. 5, there is shown a cut-away of the cuff 10 along the line 5 indicated in FIG. 2. In FIG. 5, the cuff 10 has an interior chamber 30 formed therein by RF welding together the front side sheet 102 and the back side sheet 101 to each other about their perimeters, thereby forming a seal 32 about the perimeter. The front side sheet 102 has an inner side or face 102A and an outer side or face 102B. Likewise, the back side sheet 101 has an interior side 101A and an outer side 101B.

Figure 4:
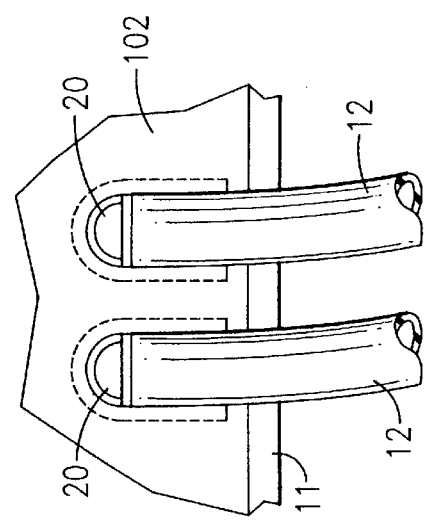
FIG. 4 is a magnified cut-away view of a tube-fitting assembly as outlined in FIG. 3.

The preferred means to inflate and deflate the cuff is to supply a pressurized fluid to the interior chamber 30 via conduit means, such as tubes 12 (FIG. 4) constructed of rubber or similar materials. As is well known in the art, the tubes 12 are usually connected at one end to a pneumatic bulb (not shown). In use, the pneumatic bulb is manually constricted by the user thereby forcing air into one of the tubes 12, and thus, the interior chamber 30. In the preferred embodiment, the conduit means includes a port fitting 20 (FIG. 4) that provides a connection between the tubes 12 and the interior chamber 30. The port fitting 20 is also RF welded to the inner surface 102A of front side 102. In conventional cuffs, the port fitting is sewn or welded into the edge of the cuff. In the present invention as shown in FIG. 4, the port fitting 20 is mounted on the front side 102 of the cuff, preferably near but not on the edge 11 of the cuff 10. This unique placement of the port fitting 20 is enabled by providing a 90 degree turn in the fittings so that the rubber tubes 12 are aligned in parallel with the plane of the front side 102. This alignment provides for efficient use of the cuff 10 and comfortable fit for the patient. In addition, this feature aids in the ease of manufacture of the cuff 10.

The cuff 10 is supplied with a sufficient amount of pressure on the artery of the patient to shut off the blood flow in the artery of the limb around which the cuff 10 is fastened. At that point, the diagnostician actuates an air release mechanism to slowly release air from the other of the tubes 12 and simultaneously listens through a stethoscope to determine the pressure at which the blood flow resumes.

As described above, the front and back sides are RF welded to each other to form the cuff 10. The RF welding of the two sheets to each other is facilitated by providing the inner sides 101A/101B of the sheets with a urethane coating thereby providing a suitable adhesive quality. As also described above, all of the components are RF welded to the outer sides 101B/102B of the cuff 10, including the hook/loop fasteners 14/16, the cleat 18, and the port fittings 20 are RF welded to the inner surface 102A. Each of the components has a urethane coating on the base portion of the component which provides suitable adhesive qualities. The port fittings 20 are made of urethane and are directly RF welded to inner surface 102A therefore needing no supplemental urethane coating. The outer sides 101B/102B of the cuff have a kiss coat of urethane which is sufficient enough to provide adhesive qualities for RF welding yet is thin enough to maintain the desired feel of the material. The preferred mode of applying the kiss coat is in the range of 0.50 ounces to 0.75 ounces of urethane per square yard of nylon fabric, or approximately less than 0.001 inches in thickness. This feature provides improved comfort to the patient and ease of handling for the diagnostician. In addition, by reducing the amount of urethane coating on the outside surfaces of the cuff 10, the cost of manufacturing is reduced.

An additional feature which can be added to the urethane coating is an antimicrobial agent or chemical. The agent is mixed with the urethane and applied during the coating process. The agent should be one which is effective in limiting the growth of bacteria, fungi and in deterring the transmittal of infectious diseases.

The cuff 10 can be manufactured in various sizes to accommodate children, adults, or very large adults. As an aid to the efficient use of the sphygmomanometer, markings 15a, 15b can be applied to the cuff 10 which indicate the proper placement of the cuff relative to the artery in the arm or leg. The markings 15a, 15b also indicate the correct diameter of the cuff when it is applied to the arm or leg so that the diameter is not too large or small to render accurate pressure measurements. The markings 15a, 15b can be applied by silk screening or other marking means known in the art.

The features of the cuff 10 make it possible for the manufacture of the cuff 10 to be highly automated. The nylon material is supplied with a coating of urethane on both sides, the outer side having a kiss coat as described above. The material is split at predetermined points by an automated slitter, the determination being made dependent upon the size of the cuff that is being manufactured. The material is then silk-screened with the desired markings at predetermined locations, which also depends upon the size of the cuff that is being manufactured. The material is supplied to an automated machine that is computer controlled. The machine is provided with material for the cleat 18, material for the hook and loop fasteners 14/16, and the port fittings 20. The machine then assembles the cuff by RF welding the front side to the back side. The machine also RF welds the components at the appropriate locations on the front and back sides of the cuff. The cuff is thereby constructed by 100% RF welding without the need for sewing, solvent bonding, or additional adhesives.

While the present invention has been particularly shown and described with reference to the preferred mode as illustrated in the drawings, it will be understood by one skilled in the art that various changes in detail may be effected therein without departing from the spirit and scope of the invention as defined by the claims.

What is claimed is:

1. An inflatable blood pressure cuff comprising:

a pair of flexible gas-impermeable sheets, each of said sheets having an inner and an outer side, wherein said inner sides are placed in contact and the edges of said sheets are fused along a periphery thereof to form an interior chamber;

at least one hook fastener portion disposed on one outer side of one of said sheets and at least one loop portion disposed on an outer side of the other of said sheets; and conduit means attached to one of said flexible sheets for connecting to a source of pressurized fluid for allowing inflation and deflation of said interior chamber, wherein said sheets are fused together by RF welding along a perimeter of one outer side of one of said sheets, and further wherein said at least one hook fastener portion, said at least one loop portion, and said conduit means are each RF welded to an outer side of one of said sheets.

2. The inflatable blood pressure cuff according to claim 1, wherein said flexible sheets comprise a fabric material.

3. The inflatable blood pressure cuff according to claim 2, wherein said fabric material is nylon.

4. The inflatable blood pressure cuff according to claim 2, wherein said fabric material has a coating, said coating comprising urethane.

5. The inflatable blood pressure cuff according to claim 4, wherein the outer side of each of said flexible sheets includes a urethane coating, said coating of the outer side having a thickness less than 0.001 inches.

6. The inflatable blood pressure cuff according to claim 5, wherein said coating further comprises an antimicrobial agent.

7. The inflatable blood pressure cuff according to claim 1, wherein said conduit means includes a port fitting attached to an outer side of one of said opposed sheets, wherein said port fitting is RF welded to the inner side of the flexible sheet.

8. The inflatable blood pressure cuff according to claim 1, including a cleat portion disposed on one outer side of one of said sheets.

9. The inflatable blood pressure cuff according to claim 1, including a cleat portion, wherein said cleat portion is RF welded to an outer side of one of said flexible sheets.

10. The inflatable blood pressure cuff according to claim 1, including a plurality of range markings disposed on one outer side of one of said sheets.

* * * * *